United States Patent [19]

Merger et al.

[11] Patent Number: 4,537,960

[45] Date of Patent: Aug. 27, 1985

[54] PREPARATION OF CARBAMATES

[75] Inventors: Franz Merger, Frankenthal; Gerhard Nestler; Friedrich Towae, both of Ludwigshafen, all of Fed. Rep. of Germany

[73] Assignee: BASF Aktiengesellschaft, Ludwigshafen, Fed. Rep. of Germany

[21] Appl. No.: 529,037

[22] Filed: Sep. 2, 1983

[30] Foreign Application Priority Data

Sep. 8, 1982 [DE] Fed. Rep. of Germany ....... 2033310

[51] Int. Cl.$^3$ ............... C07C 125/065; C07D 265/30; C07D 295/14
[52] U.S. Cl. .................. 544/86; 260/239 E; 544/58.6; 546/190; 548/523; 560/27; 560/32; 560/115; 560/159
[58] Field of Search ............... 544/86, 58.6; 546/190; 548/523; 560/159, 27, 32, 115; 260/239 E

[56] References Cited

U.S. PATENT DOCUMENTS

| | | | |
|---|---|---|---|
| 2,837,561 | 6/1958 | Beinfest et al. | 560/157 |
| 2,871,259 | 1/1959 | Levy | 560/157 |
| 3,449,406 | 6/1969 | Goodman et al. | 560/157 X |
| 3,574,711 | 4/1971 | Robeson | 560/157 |
| 3,639,455 | 2/1972 | Petersen et al. | 560/166 |
| 4,156,784 | 5/1979 | Dockner et al. | 560/157 |
| 4,436,668 | 3/1984 | Harder et al. | 260/463 |
| 4,443,622 | 4/1984 | Smith | 560/157 X |

FOREIGN PATENT DOCUMENTS 46-6042 2/1971 Japan .

OTHER PUBLICATIONS

Adams et al., Chemical Reviews, vol. 65, (10-1965), pp. 569 and 570.
Houben-Weyl, Methoden der Organischen Chemie, vol. 8, pp. 140-141 (1952).
Paquin, z. f. Naturforschung 1, 518-523, (1946).

*Primary Examiner*—Richard L. Raymond
*Attorney, Agent, or Firm*—John H. Shurtleff

[57] ABSTRACT

N- and O-substituted carbamates are prepared by reacting urea with an aminopropanol at 140° C. or above. The compounds obtained by the novel process are useful starting materials for the preparation of textile finishing agents, stabilizers, plasticizers, dyes and crop protection agents.

11 Claims, No Drawings

PREPARATION OF CARBAMATES

The present invention relates to a process for the preparation of N- and O-substituted carbamates by reacting urea with an aminopropanol at 140° C. or above.

Houben-Weyl, Methoden der Organischen Chemie, Volume 8, pages 140-141 discloses that urea can be reacted with an alcohol to give an O-substituted carbamate. Alkylation of the urea by the corresponding alcohol to give an N-substituted urea is not observed. The reaction is carried out under atmospheric pressure at the boiling point of the mixture, if appropriate using zinc acetate or stannic chloride as a catalyst. According to Paquin (Z.f.Naturforschung 1, 581-523), the yield can be increased by adding a heavy metal salt. However, the disadvantage of these methods is that various by-products, eg. biuret, allophanates, cyanic acid or carbonates, are formed in substantial amounts and the yield is correspondingly poor (German Laid-Open Application DOS No. 2,459,765).

In order to prevent the formation of these by-products, German Laid-Open Application DOS No. 1,643,635 proposes using nickel salts as catalysts. Although this method gives yields of 94%, it has not become important commercially because long reaction times are required and the carcinogenic nickel salts have to be removed from the reaction mixture by a procedure which pollutes the effluent, or this effluent has to be worked up. German Laid-Open Application DOS No. 2,459,765 proposes using nickel-containing ion exchangers as catalysts. However, the disadvantages of this process include once again the use of carcinogenic nickel salts, the expensive preparation of the catalyst by a procedure which gives a polluted effluent (German Laid-Open Application DOS No. 2,459,765, Example 1a), the formation of carbonates and the nickel compounds dissolved in the reaction mixture, which have to be removed because they are toxic.

German-Laid Open Application DOS No. 3,021,554 discloses a process for the preparation of carbonates by reacting a carbamate with an alcohol at above 140° C., wherein the ammonia formed is separated off during the reaction. The reaction is advantageously carried out in the presence of a tertiary amine or an amidine as the catalyst, or in the presence of a compound of a metal of group Ia, Ib, IIa, IIb, IIIa, IIIb, Iva, Ivb, Va, Vb, VIb, VIIb or VIIIb of the periodic table. As can be seen from the description and the Examples, no aminoalkanols are used.

We have found that N- and O-substituted carbamates of the formula

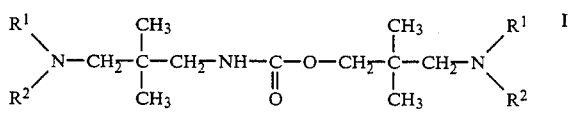

where the individual radicals $R^1$ and $R^2$ are identical or different and are each an aliphatic, cycloaliphatic or araliphatic radical, or $R^1$ and $R^2$, together with the adjacent nitrogen atom, can furthermore form a heterocyclic ring, are advantageously obtained by reacting urea with an alcohol if urea is reacted with an aminopropanol of the formula

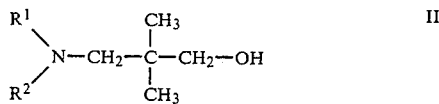

where $R^1$ and $R^2$ have the above meanings, at 140° C. or above.

Where 3-dimethylamino-2,2-dimethylpropan-1-ol is used, the reaction can be represented by the following equation:

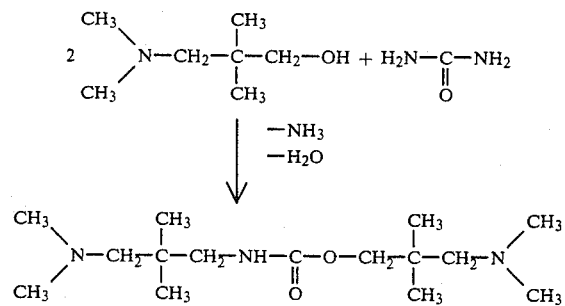

Compared with the conventional processes, the process according to the invention gives carbamates which are substituted both at the nitrogen atom and at the oxygen atom by a simpler and more economical route and in good yield, space-time yield and purity. In view of the above publications, it is surprising that the process according to the invention gives carbamates which are substituted both at the nitrogen atom and at the oxygen atom by a simple method and in good yield and purity without the use of catalysts and without the formation of substantial amounts of by-products. Particularly, with reference to German Laid-Open Application DOS No. 1,643,635, it was not to be expected that good yields or high purity would be obtained, and it was even to be expected that poorer results would be achieved, since, in contrast to the proposal of the Laid-Open Application to use only nickel salts in an amount of from 0.1 to 5% by weight, based on urea, and in contrast to the proposal of German Laid-Open Application DOS No. 2,459,765 to use cation exchangers and nickel bonded to the exchanger as cations, the novel process is carried out in the absence of a catalyst. By dispensing with catalysts and exchangers, the novel process is safer in operation, avoids toxic products and effluent problems and hence causes less pollution.

In view of German Laid-Open Application DOS No. 3,021,554, it is surprising that the special structure of aminopropanols which carry two methyl groups in the 2-position results in the formation of carbamates instead of carbonates; the above publications also did not indicate that the aminopropanols having a structure according to the invention are converted to carbamates which are substituted both at the nitrogen atom and at the oxygen atom.

Urea can be reacted with the starting materials II in a stoichiometric amount, in excess or in less than the stoichiometric amount. As a rule, the amount used where an additional solvent is employed is preferably from 0.5 to 10, in particular from 0.8 to 2, moles of starting material II per mole of urea. If the reaction is carried out in the absence of an additional solvent, ie. if the reactants themselves serve as the reaction medium, it is advantageous to use from 0.8 to 10, in particular from 1 to 5, moles of starting material II per mole of urea.

Preferred starting materials II and, accordingly, preferred end products I are those in whose formulae the individual radicals $R^1$ and $R^2$ are identical or different and are each alkyl of 1 to 18, preferably 1 to 8, in particular, 1 to 6, carbon atoms, alkenyl of 2 to 12, advantageously 2 to 6, carbon atoms, cycloalkyl of 3 to 8 carbon atoms or aralkyl of 7 to 12 carbon atoms, or $R^1$ and $R^2$, together with the adjacent nitrogen atom, can furthermore form a 3-membered to 7-membered ring which can contain a further nitrogen atom or an oxygen atom or sulfur atom. The above radicals can furthermore be substituted by groups which are inert under the reaction conditions, eg. alkyl or alkoxy, each of 1 to 4 carbon atoms.

Examples of aminopropanols which are suitable starting materials II are 2,2-dimethyl-3-dibenzyl-, 2,2-dimethyl-3-dimethyl-, 2,2-dimethyl-3-diisopropyl-, 2,2-dimethyl-3-diethyl-, 2,2-dimethyl-3-di-sec.-butyl-, 2,2-dimethyl-3-dicyclohexyl-, 2,2-dimethyl-3-dipentyl-, 2,2-dimethyl-3-dicyclopentyl-, 2,2-dimethyl-3-diphenylethyl-, 2,2-dimethyl-3-dipropyl-, 2,2-dimethyl-3-didecyl-, 2,2-dimethyl-3-di-n-octyl-, 2,2-dimethyl-3-di-tert.-butyl-, 2,2-dimethyl-3-diisobutyl-, 2,2-dimethyl-3-di-n-butylaminopropan-1-ol, N-methyl-N-phenyl-2,2-dimethyl-3-aminopropan-1-ol, 3-piperidino-, 3-morpholino-, 3-pyrrolidino-, 3-aziridino- and 3-thiomorpholino-2,2-dimethylpropan-1-ol, preferably 3-dimethylamino-2,2-dimethylpropan-1-ol, 3-dipropylamino-2,2-dimethylpropan-1-ol, 3-diethylamino-2,2-dimethylpropan-1-ol, 3-(N-ethyl-N-methyl)-amino-2-dimethylpropan-1-ol, 3-piperidino-2,2-dimethylpropan-1-ol, 3-morpholino-2,2-dimethylpropan-1-ol and 3-pyrrolidino-2,2-dimethylpropan-1-ol.

The reaction is carried out at 140° C. or above, advantageously between 140° and 260° C., preferably from 160° to 240° C., under atmospheric, superatmospheric or reduced pressure, continuously or batchwise. In general, the starting material II also serves as the medium for the reaction, but if necessary an organic solvent which is inert under the reaction conditions, eg. an aromatic hydrocarbon, such as benzene, toluene, ethylbenzene, o-, m- or p-xylene, isopropylbenzene or a mixture of these, may also be used. Advantageously, the solvent is used in an amount of from 50 to 1,000, preferably from 100 to 500, % by weight, based on starting material II. During the reaction, the pH is generally maintained at 7 or above.

The reaction can be carried out as follows: a mixture of urea and starting material II is kept at the reaction temperature for from 2 to 10 hours. The ammonia formed in the reaction can be removed from the reaction solution by distillation. Some ammonium carbamate is formed, and this can be precipitated in a downstream condenser and recycled to the urea synthesis. The reaction mixture is then cooled and filtered, and the end product is separated off from the filtrate in a conventional manner, for example by distillation.

The compounds obtainable by the process of the invention are useful starting materials in the preparation of textile finishing agents, stabilizers, plasticizers, dyes and crop protection agents. By means of thermal cleavage, isocyanates can be prepared. Regarding the use of these compounds, reference may be made to the above publications.

EXAMPLE 1

360 g of urea and 1,965 g of 3-dimethylamino-2,2-dimethylpropan-1-ol were heated at 180° C. for 7.5 hours in a stirred apparatus equipped with a condenser kept at 80° C. When the reaction was complete, the mixture was allowed to cool and 1,025 g of 3-dimethylamino-2,2-dimethylpropan-1-ol were distilled off. 770 g (74.8% of theory) of N-(3-dimethylamino-2,2-dimethylpropyl) O-(3'-dimethylamino-2',2'-dimethylpropyl) carbamate of boiling point 116°–117° C./0.5 mbar remained.

EXAMPLES 2–6

The procedure described in Example 1 was followed, except that other aminopropanols II were reacted with urea in the same molar ratio at various temperatures and for various reaction times. The results are shown in the Table.

TABLE

| Example No. | $R^1, R^2$ | Time in hours | Temperature in °C. | End product I (based on aminopropanol II converted) in % of theory |
| --- | --- | --- | --- | --- |
| 2 | ![pyrrolidino] N— | 6 | 180 | 81.3 |
| 3 | ![morpholino] O  N— | 10 | 230 | 53.7 |
| 4 | ![piperidino] N— | 7 | 210 | 69.0 |
| 5 | $-C_2H_5$, $-C_2H_5$ | 7 | 215 | 73.4 |
| 6 | $C_3H_7-$, $C_3H_7-$ | 7 | 210 | 74.8 |

We claim:

1. A process for the preparation of an N- and O-substituted carbamate of the formula

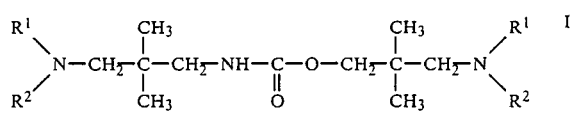

where the individual radicals $R^1$ and $R^2$ are identical or different and are each an aliphatic, cycloaliphatic or araliphatic radical, or $R^1$ and $R^2$, together with the adjacent nitrogen atom, can furthermore form a heterocyclic ring, wherein urea is reacted with an aminopropanol of the formula

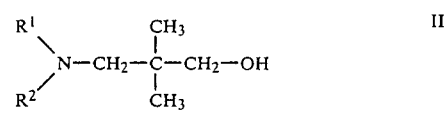

where $R^1$ and $R^2$ have the above meanings, at 140° C. or above.

2. The process as claimed in claim 1, wherein the reaction is carried out using from 0.5 to 10 moles of starting material II per mole of urea.

3. The process as claimed in claim 1, wherein the reaction is carried out in the absence of an additional solvent, using from 0.8 to 10 moles of starting material II per mole of urea.

4. A process as claimed in claim 1, wherein the reaction is carried out at between 140° and 260° C.

5. A process as claimed in claim 1, wherein the reaction is carried out at from 160° to 240° C.

6. A process as claimed in claim 1, wherein the reaction is carried out using from 50 to 1,000% by weight, based on starting material II, or an organic solvent which is inert under the reaction conditions.

7. A process as claimed in claim 1 which is carried out in the absence of a catalyst.

8. A process as claimed in claim 1 wherein a starting material II is used in which the radicals $R^1$ and $R^2$ are identical or different and are each alkyl of 1 to 18 carbon atoms, alkenyl of 2 to 12 carbon atoms, cycloalkyl of 3 to 8 carbon atoms or aralkyl of 7 to 12 carbon atoms, or $R^1$ and $R^2$ together with the adjacent nitrogen atom form a 3-to 7-membered ring which may further contain a nitrogen, oxygen or sulfur atom, and each of said radicals may be further substituted by alkyl or alkoxy, each of 1 to 4 carbon atoms.

9. A process as claimed in claim 8 which is carried out in the absence of a catalyst.

10. A process as claimed in claim 8 wherein the reaction is carried out using from 0.5 to 10 moles of starting material II per mole of urea and at a temperature between 140° to 260° C.

11. A process as claimed in claim 10 which is carried out in the absence of a catalyst.

* * * * *